United States Patent [19]

Tu

[11] 4,291,186

[45] Sep. 22, 1981

[54] TRANSALKYLATION PROCESS

[75] Inventor: Hosheng Tu, Shorewood, Ill.

[73] Assignee: UOP Inc., Des Plaines, Ill.

[21] Appl. No.: 129,940

[22] Filed: Mar. 13, 1980

[51] Int. Cl.³ .............................................. C07C 5/22
[52] U.S. Cl. ................................................. 585/475
[58] Field of Search ......................................... 585/475

[56] References Cited

U.S. PATENT DOCUMENTS 3,527,824  9/1970  Pollitzer ............................... 585/475
3,796,765  3/1974  Shioiri et al. ........................ 585/475

*Primary Examiner*—Curtis R. Davis
*Attorney, Agent, or Firm*—James R. Hoatson, Jr.; John G. Cutts, Jr.; William H. Page, II

[57] ABSTRACT

Toluene is transalkylated utilizing a catalyst comprising mordenite and arsenic.

2 Claims, No Drawings

TRANSALKYLATION PROCESS

BACKGROUND OF THE INVENTION

This invention relates to a conversion process for the transalkylation of toluene into more useful compounds. More specifically, this invention is concerned with a conversion process for the transalkylation of toluene utilizing a catalyst comprising mordenite and arsenic.

It is known in the art to effect hydrogenation of mineral oils containing aromatic hydrocarbons so as to obtain products of lower boiling range; e.g. materials in the gasoline range. For example, U.S. Pat. No. 3,197,398 (D. A. Young, issued July 27, 1965) discloses such a process where the catalyst used is a molecular sieve of the "X", "Y" or "L" crystal type containing a Group VIII metal. It is also known in the field of catalytic hydrogenation that arsenic acts as a poison or inhibitor of a large number of catalysts in numerous types of reactions. In the text "Catalysis" by Berkman, Morrell, and Egloff (Reinhold, 1940) it is reported at page 393 that arsenious oxide "due to its reduction to arsine, is a strong poison for catalytic hydrogenation with platinum as a catalyst."

The U.S. Pat. No. 3,832,307 teaches that hydrocarbons such as mineral oils containing aromatic components are effectively hydrogenated to a hydrocarbon composition of less aromaticity and greater saturation by use of a hydrogenation catalyst consisting of a "Y" type zeolite molecular sieve which contains arsenic.

The U.S. Pat. No. 3,527,824 teaches the transalkylation of toluene utilizing a catalyst comprising a crystalline aluminosilicate, a Group VIII metal and arsenic.

OBJECTS AND EMBODIMENTS

A specific object of the present invention is to provide a novel method for transalkylating toluene to provide the desired benzene and xylene in high yields.

One embodiment of this invention relates to a transalkylation process which comprises contacting toluene at transalkylation conditions including a temperature in the range of from 400° C. to about 520° C., a pressure in the range of from about atmospheric to about 100 atmospheres, a hydrogen to hydrocarbon mole ratio of from about 2:1 to about 20:1 with a catalyst comprising mordenite and arsenic.

Other objects and embodiments will be found in the following further detailed description of my invention.

DETAILED DESCRIPTION OF THE INVENTION

The catalyst employed in my invention consists essentially of a support comprising mordenite and arsenic. The arsenic is present in an amount of from about 0.1 to about 5 weight percent based on the mordenite. The mordenite crystal structure is highly siliceous in nature and generally characterized by a silica-alumina mole ratio of from about 6 to about 12 as found in nature. The mordenite crystal structure comprises four- and five-membered rings of the $SiO_4$ and $AlO_4$ tetrahedra so arranged that the crystal lattice comprises pores and channels running parallel along the crystal axis to give a tubular configuration. This structure is unique amony the crystalline aluminosilicates since the channels or tubes do not intersect, and access to the cages or cavities is in only one direction. For this reason, the mordenite structure is frequently referred to as two-dimensional. This is in contrast to other wellknown crystalline aluminosilicates, for example faujasite, in which the cavities can be entered from three directions. Mordenite, clinoptilolite, or mordenite which has been synthesized or acid extracted, caustic extracted or otherwise treated to increase the silica-alumina mole ratio to about 20:1 or more while maintaining the mordenite crystal structure, may be used in the manufacture of the catalytic composite of this invention.

Crystalline aluminosilicates having a mordenite crystal structure have heretofore been utilized composited with a refractory inorganic oxide, typically alumina, as a hydrocarbon conversion catalyst, and are particularly useful with respect to the transalkylation of alkylaromatic hydrocarbons. It is an object of this invention to present a new and useful method of manufacture providing a novel catalytic composite with a combination of improved activity and selectivity.

The arsenic containing catalyst may suitably be prepared from commercially available mordenite such as Norton Zeolon H. The mordenite may be admixed with a non-zeolitic refractory inorganic oxide or gel. Refractory inorganic oxides for use in accordance with the method of this invention include the naturally occurring as well as the synthetically prepared non-zeolitic refractory inorganic oxides. Suitable refractory inorganic oxides are for example alumina, silica, zirconia, titania, thoria, boria, magnesia, chromia, stannic oxide and the like as well as combinations and composites thereof, for example alumina-silica, alumina-titania, etc. Alumina is a preferred refractory inorganic oxide for use herein, particularly with respect to the manufacture of a catalytic composite for use in the transalkylation of alkylaromatic hydrocarbons. The alumina may be any of the various hydrous aluminum oxides or alumina gels such as alpha-alumina monohydrate of the boehmite structure, alphaalumina trihydrate of the gibbsite structure, and beta-alumina trihydrate of the bayerite structure.

The concentration of the mordenite may be as high as 100% or the mordenite may comprise a matrix which contains a nonzeolitic refractory inorganic oxide or gel as hereinabove described. The concentration of mordenite, for example, in an alumina matrix is preferably less than about 40 weight percent of the alumina although in some cases greater concentrations may also be suitable. Concentrations of mordenite of about 20 weight percent or less are especially preferred.

The arsenic may be incorporated with the mordenite in any convenient manner including ion-exchange or impregnation. The preferred method for the incorporation of arsenic is to impregnate the mordenite with aqueous solution of an arsenic compound such as arsenic pentoxide at elevated temperatures ranging from about 100° F. to about 300° F. for up to several hours. The resulting arsenic containing mordenite is then dried and calcined.

The amount of arsenic on the mordenite may vary from about 0.1% to about 5% by weight based on mordenite. The amount of arsenic on the support is readily controlled by the amount of arsenic pentoxide in the aqueous treating medium and by the time of treatment, which techniques are known in the art.

The following examples are presented in illustration of the method of the present invention and are not intended as an undue limitation on the generally broad scope of the invention as described in the appended claims.

EXAMPLE 1

In this example, a catalytic composite of mordenite and alumina was prepared with subsequent ammoniacal treatment which represents a prior method of catalyst preparation. Equal weights on a volatile free basis of a commercial mordenite (H Zeolon) and a commercial alpha-alumina monohydrate (Catapal medium) were thoroughly mixed with the addition of a 5.5 weight percent $HNO_3$ solution in a continuous mixer. The resulting dough was extruded and calcined thereafter on a belt calciner at 300° F. for one hour and at 900° F. for two hours.

The resulting calcined extrudate was immersed in a 15 weight percent ammonia solution in a glass rotary evaporator. The extrudate was then dried and subsequently calcined on a belt calciner at 550° F. for one hour and at 1100° F. for two hours. This catalytic composite was coded TA-1.

EXAMPLE 2

In this example, 100 grams of TA-1 from Example 1 were impregnated to 0.045 weight percent in a glass rotary evaporator. The impregnation solution consisted of 0.14 grams of $As_2O_5$ dissolved in 300 milliliters of 15 weight percent ammonia solution. The catalyst and the solution were cold rolled for one hour in the glass evaporator and then heated to evaporate the ammonia solution. The catalyst containing arsenic was then calcined for one hour at 550° F. and for two hours at 1100° F. This catalyst was coded TA-2.

EXAMPLE 3

In this example, TA-1 (the control sample) and TA-2 (the arsenic attenuated catalyst) were tested in a small scale toluene transalkylation plant. The test conditions included a reactor pressure of 400 psig, and a weight hourly space velocity of 1.2. The reactor temperature was adjusted to yield 40 percent toluene conversion and indicated the relative activity. The feedstock consisted of 99.9 weight percent toluene and 8 ppm non-aromatics in the benzene boiling range.

The control sample, TA-1, required a temperature of 739° F. to achieve 40% conversion of the toluene, has an aromatic ring loss of 1.29 mole percent and the hydrocarbon product contained 14,600 ppm non-aromatics in the benzene boiling range. The arsenic attenuated catalyst, TA-2, required a lower temperature of only 720° F. to attain 40% conversion of the toluene which indicates a higher activity, had an aromatic ring loss of only 0.51 mole percent and the hydrocarbon product contained only 330 ppm non-aromatics in the benzene boiling range.

The results of these two comparative catalyst tests are summarized in Table I.

TABLE I

| Toluene Transalkylation Summary | | |
|---|---|---|
| Catalyst | TA-1 | TA-2 |
| Temperature for 40 mole % conversion, °F. | 739 | 720 |
| Mole % aromatic ring loss at 40% conversion | 1.29 | 0.51 |
| PPM non-aromatics in benzene boiling range | 14,600 | 330 |

Significant performance improvement for TA-2 catalyst having arsenic attenuation is observed in comparison to the control catalyst, TA-1. The activity for toluene conversion is better, while the selectivity to undesirable by-products is greatly improved.

The foregoing specification, and particularly the examples, indicate the method by which the present invention is effected, and the benefits afforded through the utilization thereof.

I claim as my invention:

1. A transalkylation process which comprises contacting toluene at transalkylation conditions including a temperature in the range of from about 400° C. to about 520° C., a pressure in the range of from about atmospheric to about 100 atmospheres, a hydrogen to hydrocarbon mole ratio of from about 2:1 to about 20:1 with a catalyst consisting essentially of mordenite, alumina and arsenic.

2. The process of claim 1 wherein said arsenic is present in an amount from about 0.1 weight percent to about 5 weight percent based on mordenite.

* * * * *